(12) United States Patent
Menzel et al.

(10) Patent No.: US 9,249,069 B2
(45) Date of Patent: Feb. 2, 2016

(54) METHOD FOR REMOVING HIGH-BOILING HYDROCARBONS FROM SOLVENT FLOWS

(75) Inventors: Johannes Menzel, Waltrop (DE); Holger Thielert, Dortmund (DE)

(73) Assignee: THYSSENKRUPP UHDE GMBH, Dortmund (DE)

( * ) Notice: Subject to any disclaimer, the term of this patent is extended or adjusted under 35 U.S.C. 154(b) by 227 days.

(21) Appl. No.: 13/885,935

(22) PCT Filed: Nov. 11, 2011

(86) PCT No.: PCT/EP2011/005676
§ 371 (c)(1),
(2), (4) Date: Jul. 25, 2013

(87) PCT Pub. No.: WO2012/065703
PCT Pub. Date: May 24, 2012

(65) Prior Publication Data
US 2014/0323790 A1  Oct. 30, 2014

(30) Foreign Application Priority Data

Nov. 16, 2010 (DE) .......................... 10 2010 051 396

(51) Int. Cl.
*C07C 7/08* (2006.01)
*C10G 21/28* (2006.01)
*C07C 7/00* (2006.01)
*C10G 21/06* (2006.01)

(52) U.S. Cl.
CPC . *C07C 7/005* (2013.01); *C07C 7/08* (2013.01); *C10G 21/06* (2013.01); *C10G 21/28* (2013.01); *C10G 2300/4081* (2013.01); *C10G 2300/44* (2013.01); *C10G 2300/805* (2013.01)

(58) Field of Classification Search
None
See application file for complete search history.

(56) References Cited

U.S. PATENT DOCUMENTS

| 4,081,355 | A | 3/1978 | Preusser et al. |
| 4,997,547 | A | 3/1991 | Emmrich et al. |
| 5,877,385 | A | 3/1999 | Lee et al. |
| 8,362,314 | B2 | 1/2013 | Stabel et al. |
| 2009/0038991 | A1 | 2/2009 | Wu et al. |
| 2009/0105514 | A1 | 4/2009 | Lee et al. |

FOREIGN PATENT DOCUMENTS

| EP | 0329958 | 8/1989 |
| WO | 2009043753 | 4/2009 |

OTHER PUBLICATIONS

International Search Report for PCT/EP2011/005676, English translation attached to original, Both completed by the European Patent Office on Feb. 10, 2012, All together 7 Pages.

*Primary Examiner* — Tam M Nguyen
(74) *Attorney, Agent, or Firm* — Brooks Kushman P.C.

(57) ABSTRACT

A method for removing high-boiling hydrocarbons from water-soluble solvent flows, wherein said solvent flows are produced in industrial processes which circulate a solvent as a part of the process, and the solvent must be periodically or permanently freed of high-boiling hydrocarbons which influence the quality or the desired properties of the solvent in an unwanted way, and water is added for carrying out the method in a phase separator, so that the high-boiling hydrocarbons are separated off because of their immiscibility with water, and then the water-miscible phase containing water and solvent is returned to the process. According to the invention, the proportion of high-boiling hydrocarbons in circulating solvents in an industrial process can be kept permanently low.

5 Claims, 2 Drawing Sheets

METHOD FOR REMOVING HIGH-BOILING HYDROCARBONS FROM SOLVENT FLOWS

CROSS-REFERENCE TO RELATED APPLICATION

Figure 1:
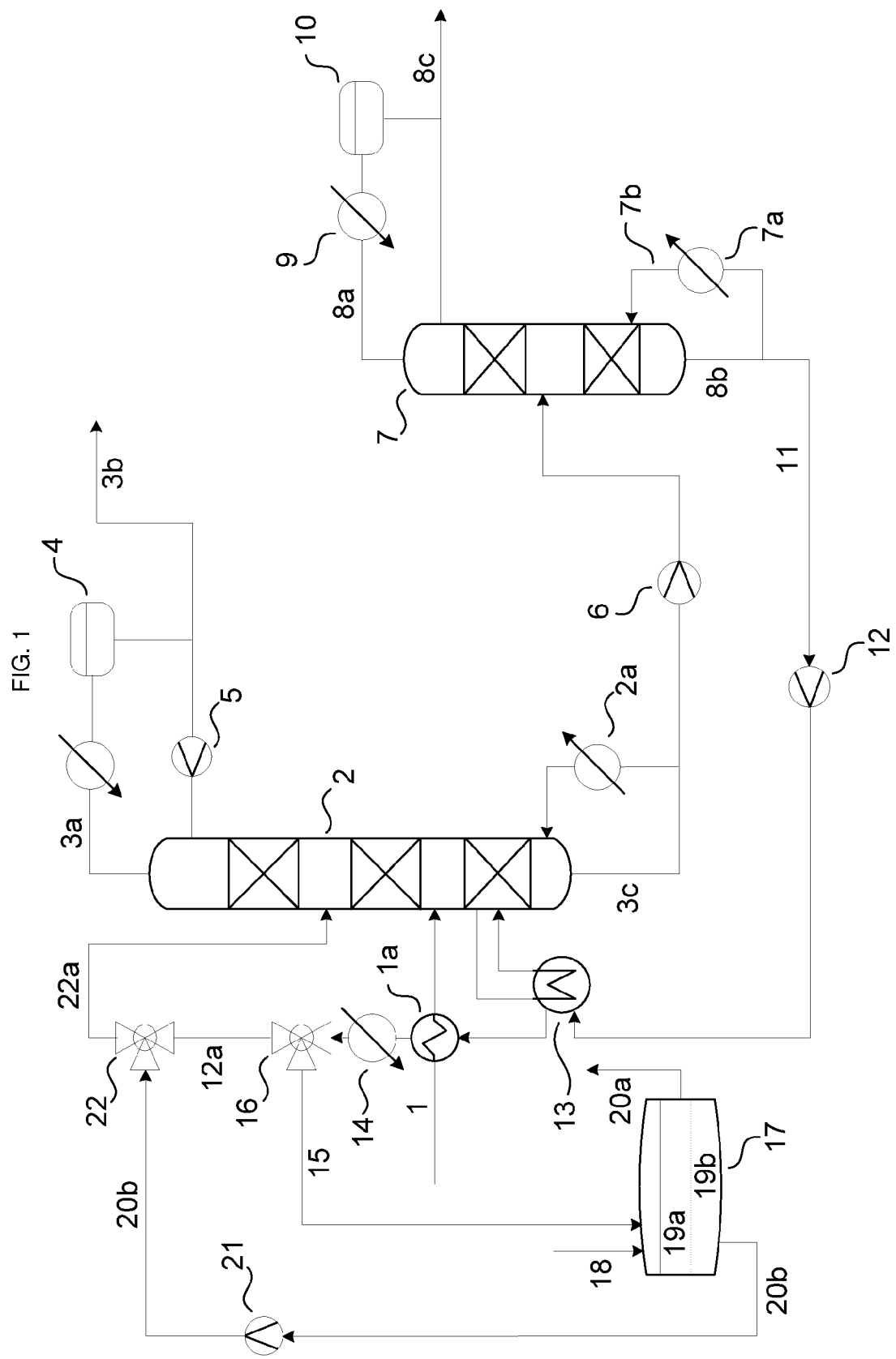

This application is the U.S national phase of PCT Appln. NO. PCT/EP2011/005676 filed on Nov. 11, 2001, which claims priority to German Patent Appln. No. 10 2010 051 396.2 filed on Nov. 16, 2010, the disclosures of which are incorporated in their entirety by reference herein.

The invention relates to a process for the removal of high-boiling hydrocarbons from water-soluble solvent streams, with these solvent streams being obtained in industrial processes, in which a solvent is circulated as constituent of the process, which is to be freed periodically or permanently from high-boiling hydrocarbons that have a detrimental impact on the quality or the desired properties of the solvent, and with water being added to a phase separator for running the process, the high-boiling hydrocarbons thus being separated on account of their immiscibility with water, and the water-mixable phase containing water and solvent then being returned to the process. The inventive process allows keeping the portion of high-boiling hydrocarbons contained in circulated solvents in an industrial process permanently low.

Many industrial processes use solvents for running the process, with the solvents being an integral part of the process, being circulated and required because of their properties for conducting the reaction. Typical processes are, for example, extractive distillations and gas treatment processes. As the solvents are frequently used for the treatment of hydrocarbonaceous feedstocks, existing high-boiling hydrocarbon constituents from the starting mixture accumulate in the solvent streams and frequently have a detrimental impact on their properties in an undesirable manner.

The accumulation of high-boiling hydrocarbons in solvents has a detrimental impact on many processes. For example, the presence of these compounds, which may originate from both the group of paraffinic compounds and of cyclic or aromatic compounds, can cause the solvent to start foaming. It can also happen that the separation efficiency of the solvent decreases when the accumulation reaches a correspondingly high level. The accumulation of heavy hydrocarbons may cause that the required product quality can no longer be met.

A separation by simple distillation will only be possible in some cases if, for example, the boiling point differences allow such separation and no azeotropic mixtures will be formed. A distillation incurs high costs or can, on account of the low boiling point differences, only be performed at high technical expenditure with the solvents used. Frequently, thermal separation is almost impossible since the solvent decomposes at an increased temperature and in the presence of higher water concentrations. Therefore, ways have to be found to separate the high-boiling hydrocarbons in a simple way from the solvents used in a technical process.

There are state-of-the-art processes hereto which remove the unwanted high-boiling components from the process on account of their immiscibility with water. As a result, an energy-intensive distillation for the removal of these constituents is not required. After the addition of water major part of the solvent which can at least partially be mixed with water changes to the aqueous phase, whereas the high-boiling hydrocarbon completely changes to the phase which cannot be mixed with water. This phase is then separated and discarded or the unwanted high-boiling component is removed by simple distillation from the phase which cannot be mixed with water. Major part of the solvent changes to the aqueous phase depending on the miscibility. This phase is then distilled for removing the water and the solvent is returned to the process.

EP 0329958 A2 describes a process for the manufacture of an aromatics concentrate suitable for use as a blending component for carburettor fuels, with feed column hydrocarbon mixtures, the boiling range of which is essentially between 40° C. and 170° C., being subjected, without previous separation into individual fractions, to an extractive distillation using N-substituted morpholines, the substituents of which contain not more than seven C atoms, as the selective solvent, such that virtually all the low-boiling non-aromatics having a boiling range of up to about 105° C. and the predominant part of the higher-boiling non-aromatics having a boiling range between about 105° C. and 160° C. are extracted as a refined product, whereupon the aromatics which are used wholly or partially as a blending component are found in the extract from the extractive distillation, and for the separation of heavy aromatics from the solvent a partial stream of the circulated solvent is mixed with water, and the heavy aromatics are separated as light phase from the solvent/water mixture which is subsequently separated into its constituents and re-used in the process. The re-processing step is energy-intensive and therefore involves high costs.

WO 2009043753 A1 teaches a process for obtaining aromatic hydrocarbons, selected from benzene, toluene, xylene and ethyl benzene and mixtures thereof, from a hydrocarbon mixture which in addition contains non-aromatic hydrocarbons and high-boiling components, with an extractive distillation using an extractive solvent being provided as purification step for the aromatic hydrocarbons, and a partial stream being separated from the extractive solvent for separating the unwanted high-boiling components, and the partial stream of the extractive solvent being extracted using water, so that an aqueous extract phase that is essentially devoid of high-boiling components and an organic phase containing the high-boiling components are obtained, and the aqueous extract phase is distilled for recovering the extractive solvent in a purified form such that the extractive solvent is returned to the extractive distillation, and with a distillation being carried out prior to conducting the extraction of the partial stream using water, a distillation in which a fraction of very high-boiling hydrocarbons is separated from the partial stream of the extractive solvent. The process is characterised in that the extractive solvent must be distilled for being recovered or discharged from the process in a time-consuming way, thus resulting in high costs. The additional distillation step for removing the high-boiling hydrocarbons from the extractive solvent prior to adding water results in additional energy costs.

It would therefore, be of advantage to provide a process which unmixes the high-boiling hydrocarbons via formation of two phases by adding water to a partial stream of an extractive solvent, which removes the high-boiling and water-insoluble hydrocarbons by separating the water-insoluble organic phase, and which makes it unnecessary to further process the water-soluble phase or the phase which cannot be mixed with water by carrying out distillations. The state-of-the-art distillations are characterised by high energy expenditure and have a detrimental impact on the economic efficiency of the process.

It is therefore the objective to provide a process which allows the treatment of solvents used in industrial processes by the separation of a partial stream of the solvent used, an addition of water and phase formation, with the unwanted high-boiling hydrocarbons being separated from the process by separation of the phase which cannot be mixed with water, and further treatment of the aqueous phase from the process requiring little expenditure only.

The invention achieves the objective by a process which separates a partial stream from the industrial process that uses a solvent from which the heavy hydrocarbons must be separated, adds water to this partial stream, provides a mixing ratio with water in such a way that two phases are formed which cannot be mixed with each other, carries out a phase separation, removes the phase that cannot be mixed with water and contains the unwanted high-boiling components, returns the water-mixable phase containing the solvent to the process, with recirculation taking place in such a way that further treatment of the solvent is not required.

Typical processes where the inventive process is applied are extractive distillations or gas scrubbing processes using absorbing solvents. The aqueous phase, which contains a large part of the solvent after phase separation depending on the miscibility, is returned to the process without further treatment, the recirculation ratio being selected in such a manner that the allowable water concentration in the solvent is not exceeded. Since water is a low-boiling component, the water supplied to the solvent circuit is discharged in dependency of time via one of the process steps provided in the solvent circuit. In an extractive distillation, this can be the regenerative distillation, for example. By this method, the water concentration in the process can be kept permanently low.

Claim is particularly laid to a process for the removal of high-boiling hydrocarbons from water-soluble solvent streams in an industrial process, in which a partial stream is withdrawn from a solvent containing accumulated high-boiling hydrocarbons and fed to a tank, and water is added to this partial stream of solvent resulting in the formation of an aqueous and a non-aqueous phase, and the hydrocarbonaceous phase is separated and withdrawn from the tank, and which is characterised in that the aqueous phase of adequate concentration is returned to the process without further distillation.

The tank can be of any type. This can be a simple tank which is suited for the fractionation and separation of phases which cannot be mixed with each other. But it can also be an extractor which discharges both phases separately, the phase mixable with water being intermediately stored if required in order to be able to return this phase in a suitable concentration to the process. The tank can also be designed as a phase separator or further phase separators can be intermediately connected prior to the introduction to the process to ensure complete phase separation.

The process for the removal of high-boiling hydrocarbons from water-soluble solvent streams is an extractive distillation, for example. The process for the removal of high-boiling hydrocarbons from solvent streams is a gas scrubbing process, for example, for the separation of unwanted gases from a gas mixture. An example of a suitable extractive distillation process is given in EP 0792928 B1. An example of a suitable gas scrubbing process is given in EP 1606041 B1. Eventually all process types are possible in which high-boiling substances accumulate in a solvent and have to be removed.

The water is added in such an amount that allows good phase separation, typically being added to the partial stream of solvent in the tank in an amount of 5 to 90 wt.-%. In an embodiment of the invention the tank for phase separation is equipped with a cooler with the aid of which the temperature can be reduced to ensure efficient removal of the high-boiling hydrocarbons. For the same purpose the tank for phase separation can also be equipped with a heating device.

In an embodiment of the invention the water concentration of the solvent, from which the high-boiling hydrocarbons have been separated, is 1 to 5 wt.-% directly after recirculation of the solvent to the process. In a further embodiment the water concentration of the solvent from which the high-boiling hydrocarbons have been separated is 0.5 to 2 wt.-% directly after recirculation of the solvent to the process. This allows recirculating the water to the process without any detrimental impact on the solvent. The water concentration in the process, in the phase separator or in the feed lines can, for this purpose, be occasionally or permanently determined by suitable measuring devices.

In an embodiment of the process the aqueous phase is continuously metered to the solvent circuit upon recirculation to the solvent process in such a manner that the water concentration of the solvent from which the high-boiling hydrocarbons have been separated is less than 0.5 wt.-% directly after recirculation to the process.

The water added is passed to the solvent circuit and, according to the invention, time-dependently discharged in the further process flow via process steps already provided in the solvent circuit. In the case of an extractive distillation, the excess water is typically withdrawn via the head fraction of the regeneration column for separation of the solvent (stripping column). This means that the water is removed by means of the distillation columns or regeneration columns provided for extractive distillation after the recirculation to the solvent process.

In the case of a gas scrubbing process, the excess water is in practice absorbed by the normally dry feed gas. In countercurrent flow, the feed gas supplied to the bottom of the absorption column absorbs the water contained in the solvent and supplied to the head of the absorption column theoretically up to the absorption limit, and the hence water-enriched product gas leaves the absorption column at the top. This means that the water is removed after the recirculation to the solvent process by a dry feed gas stream flowing through the absorption column.

The invention has the advantage to allow easy separation of high-boiling substances from solvent mixtures without the need for an energy-intensive and thus economically disadvantageous distillation of the solvent. The water content of the solvent in the process is kept low by suitable measures and the high-boiling compounds and hydrocarbons are withdrawn from the process. In doing so, the properties of the solvent are almost completely preserved during the operating period of the process.

Figure 2:
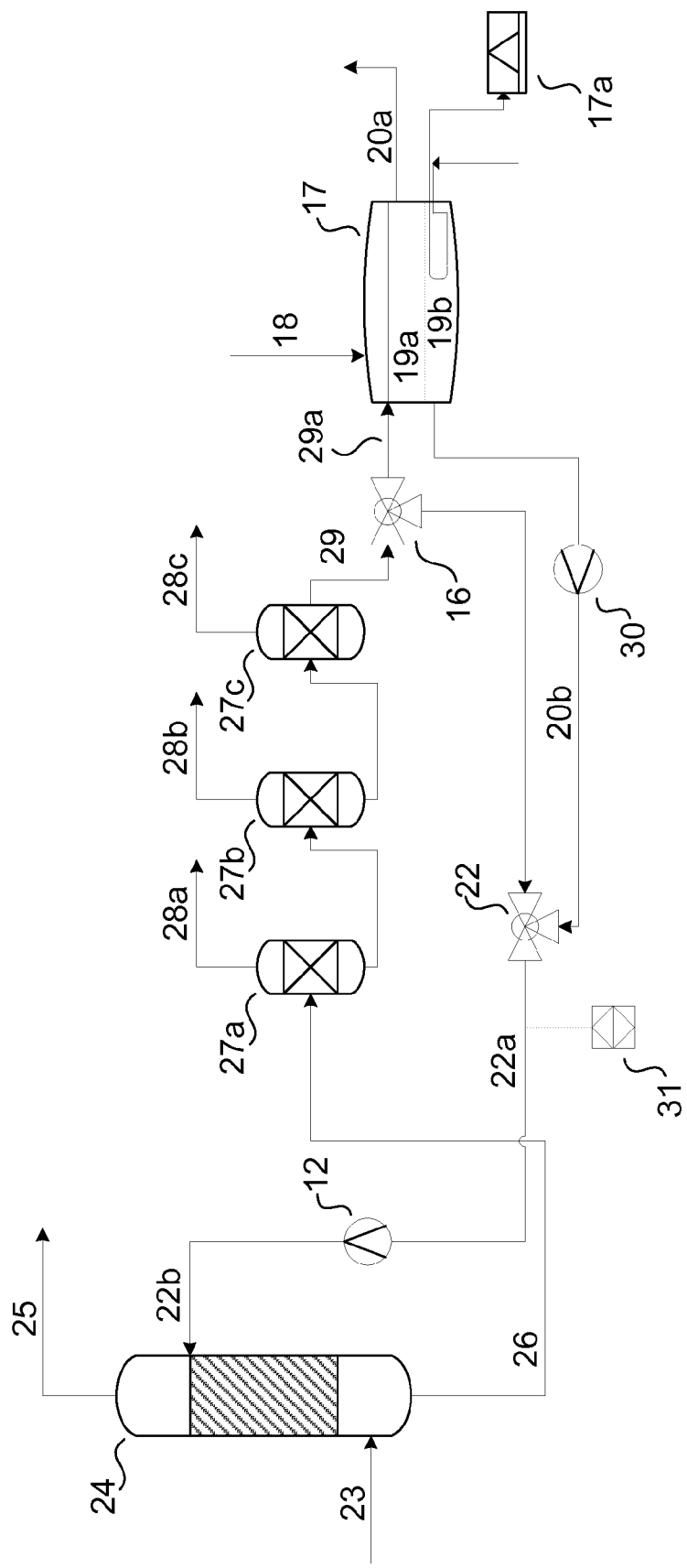

The process flow of the inventive process is described in more detail by means of two drawings, the inventive process not being limited to these embodiments. FIG. 1 shows an extractive distillation unit equipped including a tank for the addition of water and a phase separator. FIG. 2 shows a gas scrubbing unit equipped with a tank for the addition of water and a phase separator.

FIG. 1 shows the process flow for the extractive distillation of a hydrocarbon mixture with the hydrocarbonaceous feed mixture (1) being fed to a column (2) for extractive distillation. The extractive distillation column (2) is equipped with a reboiler (2*a*). This yields a material flow (3*a*) enriched with light distillation products at the head of the column. The product is returned via a reflux tank (4) and a reflux pump (5) to the head of the extractive distillation column. A partial stream (3*b*) which also contains the discharged water in a low concentration is withdrawn as product. At the bottom of the column a distillation bottom stream (3c) is obtained which contains aromatic and high-boiling hydrocarbons as well as the extracting solvent. This stream is pumped via a bottom stream pump (6) to the regeneration column (7) which is designed as a distillation column. There, at the head of the column (8a), the desired product is obtained which consists of aromatic hydrocarbons and, at the bottom of the column (8b), the solvent is obtained. The regeneration column (7) for the distillation of the solvent yields the desired product from the extractive distillation. This product is discharged (8c) via a cooler (9) and a reflux tank (10). The said product still contains the high-boiling hydrocarbons. The regeneration column (7) is also equipped with a reboiler (7a) for heating the distillation stream (7b). The solvent (8b) is re-fed to the column (2) for extractive distillation. This stream (11) is returned to the extractive distillation column (2) via a pump (12), a lateral reboiler (13) for the partial evaporation of the solvent in the extractive distillation column, a heat exchanger for heating the feed mixture (1a) and a cooler (14). A partial stream (15) of the cooled solvent stream is branched off via a valve (16) and fed to a phase separator tank (17) where water (18) is added. In doing so, two phases which cannot be mixed with each other (19a,19b) are formed. The lighter phase (19a) normally contains the high-boiling hydrocarbons and is separated and removed from the process (20a). This phase can be further processed when the need arises or used, for example, for heating purposes. The heavier phase (19b) containing the treated solvent is also separated (20b) and by means of a pump (21) returned to the process (22a) via the valve (22) together with the untreated partial stream (12a).

FIG. 2 shows a gas scrubbing process in which a feed gas (23) is brought into contact with an absorbing solvent in an absorption column (24) the unwanted sour gases being separated from the feed gas (23). In doing so, a treated product gas (25) is obtained for downstream processing. The absorbed sour gas mixed with the absorbing solvent (26) is discharged from the absorption column (24) and routed to a cascade of flash tanks (27a-c). The sour gas (28a-c) contained is stripped from the solvent (26) by successive pressure reduction. The said gas is withdrawn from the process and passed to a further process step if required. In this way, a regenerated solvent (29) is obtained. A partial stream of the regenerated solvent (29a) is branched off via a valve (16) and fed to a phase separator tank (17) where water (18) is added. In doing so, two phases (19a, 19b) are obtained. The lighter phase (19a) is separated and removed from the process (20a). This phase can be further processed when the need arises or used, for example, for heating purposes. The heavier phase (19b) is separated (20b) and, if required, returned as treated solvent (22a) to the absorption column (24) by means of a pump (30) via the valve (22). The regenerated solvent (22b) is conveyed to the head of the absorption column by means of a recycle pump (12). Here, the phase separator tank (17) is cooled by means of a cooler (17a). The feed line of the regenerated solvent (21a) to the absorption column (24) is equipped with an analytical instrument (31) for determining the water concentration.

LIST OF REFERENCE NUMBERS AND DESIGNATIONS

1 Feed mixture
1a Pre-heater or heat exchanger for feed mixture
2 Column for extractive distillation
2a Reboiler for extractive distillation column
3a Material flow at head of column for extractive distillation
3b Head stream from column for extractive distillation
3c Distillation bottom stream
4 Reflux tank
5 Reflux pump
6 Bottom stream pump for column for extractive distillation
7 Regeneration column
7a Reboiler for regeneration column
7b Distillation stream
8a Head product of regeneration column
8b Regenerated solvent bottom stream of regeneration column
8c Discharged aromatics-containing distillation product
9 Cooler for regeneration column head product
10 Reflux tank
11 Regenerated solvent stream
12 Pump for regenerated solvent
12a Main route of solvent circuit
13 Lateral reboiler
14 Cooler
15 Solvent stream containing heavy hydrocarbons
16 Valve
17 Phase separator tank
17a Cooler
18 Water
19a Lighter phase
19b Heavier phase
20a High-boiling hydrocarbons
20b Input water-containing phase containing solvent
21 Pump
22 Valve
22a Circulated stream of regenerated solvent
22b Circulated stream of regenerated solvent
23 Feed gas
24 Absorption column
25 Treated product gas
26 Sour gas-containing solvent stream
27a-c Flash tank
28a-c Sour gas streams
29 Regenerated solvent
29a Partial stream of regenerated solvent
30 Pump
31 Analytical instrument for determining the water concentration

The invention claimed is:

1. A process for the removal of high boiling hydrocarbons from water-soluble solvent streams in an industrial process which comprises a gas scrubbing process utilizing an absorbtion column and a scrubbing medium comprising a water-soluble solvent, the process comprising:
  withdrawing a partial stream of the water-soluble solvent containing accumulated high boiling hydrocarbons from the absorbtion column;
  feeding said partial stream of water-soluble solvent and water to a tank, wherein an aqueous phase, and a non-aqueous hydrocarbonaceous phase containing high boiling hydrocarbon are formed;
  withdrawing the non-aqueous hydrocarbonaceous phase from the tank;
  recirculating the aqueous phase from the tank to the water-soluble solvent used in the gas scrubbing process, at a recirculation ratio such that an allowable water concentration in the water-soluble solvent is not exceeded, the aqueous phase not having been subjected to distillation prior to recirculation,
  combining the recirculating aqueous phase from the tank with a further partial stream of solvent containing high boiling hydrocarbons such that the combined streams have a water concentration below 0.5 wt. %; and removing water after said step of recirculating by contact with a dry feed gas stream input into the absorbtion column.

2. The process for the removal of high-boiling hydrocarbons from solvent streams according to claim 1, wherein water in an amount of 5 to 90 wt.-% is added to the partial stream of water-soluble solvent in the tank.

3. The process for the removal of high-boiling hydrocarbons from solvent streams according to claim 1, further comprising cooling the tank with a cooler.

4. The process for the removal of high-boiling hydrocarbons from solvent streams according to claim 1, wherein the tank for phase separation is equipped with a heating device.

5. The process of claim 1, wherein the water content of the water-soluble solvent is monitored, and the amount of aqueous phase which is recirculated is adjusted to keep the water content below 0.5 wt. %.

* * * * *